Figure 1:
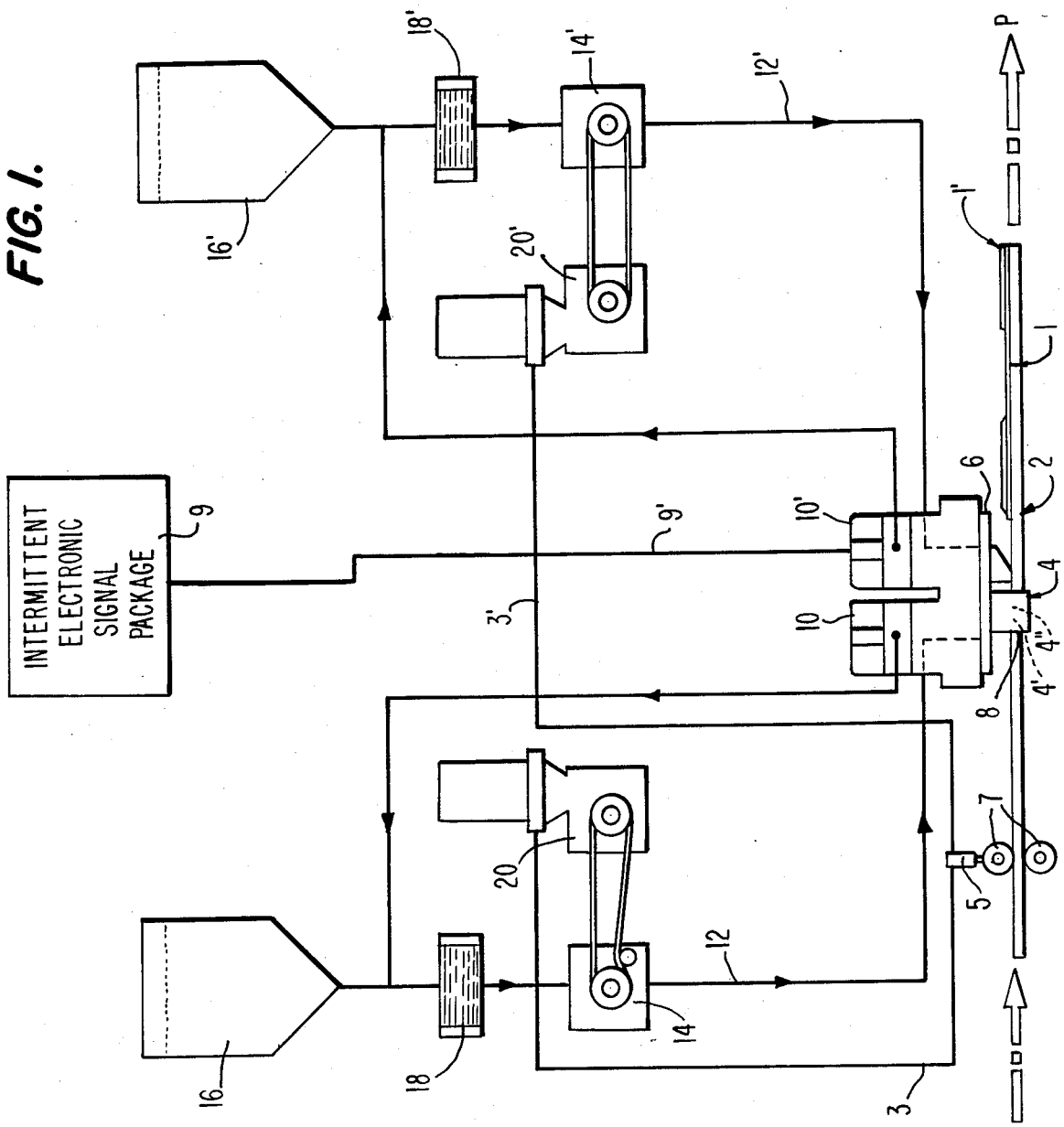

United States Patent [19]

McIntyre

[11] Patent Number: 4,725,468
[45] Date of Patent: Feb. 16, 1988

[54] METHOD OF CO-EXTRUSION OF DIFFERENT COATING MATERIALS, INCLUDING ADHESIVE COATING WITH INTERMITTENT NON-ADHERING SECTIONS, AND PRODUCTS PRODUCED THEREBY

[75] Inventor: Frederic S. McIntyre, Wellesley, Mass.

[73] Assignee: Acumeter Laboratories, Inc., Norfolk, Mass.

[21] Appl. No.: 826,594

[22] Filed: Feb. 6, 1986

[51] Int. Cl.[4] .................. A61F 13/16; A61F 13/18; A61F 13/02; E04F 15/16
[52] U.S. Cl. ..................................... 428/40; 118/698; 156/744.11; 156/500; 427/208.4; 427/208.8; 428/41; 604/385 A
[58] Field of Search ............... 156/244.11, 500; 118/698, 324; 427/208.4, 208.8, 208.6; 428/40, 41; 604/385.2

[56] References Cited

U.S. PATENT DOCUMENTS

| | | | |
|---|---|---|---|
| 3,595,204 | 7/1971 | McIntyre | 118/8 |
| 4,081,301 | 3/1978 | Buell | 156/164 |
| 4,339,485 | 7/1982 | Shibano et al. | 427/208.4 X |
| 4,476,165 | 10/1984 | McIntyre | 427/258 |
| 4,547,243 | 10/1985 | Brody | 604/385.2 |

*Primary Examiner*—Michael R. Lusignan
*Attorney, Agent, or Firm*—Rines and Rines; Shapiro and Shapiro

[57] ABSTRACT

A method of and apparatus for co-extruding upon a first continuous coating adhered to a substrate band (such as a pressure-sensitive adhesive), periodic top coat sections of coating material of different characteristics (such as non-stick properties), as for such purposes as providing laminating adhesive strips in desired regions only, as for use in diaper laminates and the like.

3 Claims, 3 Drawing Figures

METHOD OF CO-EXTRUSION OF DIFFERENT COATING MATERIALS, INCLUDING ADHESIVE COATING WITH INTERMITTENT NON-ADHERING SECTIONS, AND PRODUCTS PRODUCED THEREBY

The present invention relates to methods, apparatus and products involving the metered applicating or coating of adhesive and other coating fluids, hot melt, and other materials, by extrusion upon a strip or band of material or other web surface or substrate (hereinafter generically referred to as "band"). The invention is more particularly, though not exclusively, directed to such applicating by co-extrusion of different coating materials, as for the purpose of providing successive sections of different coating characteristics, such as adhesive and non-adhering coating strip sections on a band for such purposes, for example, as providing adhesion to an elastic band in a diaper or the like at desired central sections only of the diaper.

The latter specific diaper elastic band problem has earlier been addressed by intermittently applying adhesive to an elastic web substrate extending longitudinally along the center of the diaper so as to enable permanent attachment by lamination to a polyethylene or other web outer covering layer, only at the pressure-sensitive adhesive section, thus intermittently coated (U.S. Pat. No. 4,081,301). Suitable intermittent slot nozzle systems are described in U.S. Pat. Nos. 3,595,204 and 4,476,165. While an admirable solution to this problem, the intermittent coating technique only permits the characteristics (adhesion) of the coating to be alternated with the inherent physical characteristics of the elastic or other substrate on which it is deposited, which cannot be altered by this technique. Where it is desired to alternate the adhesive sections with sections of different, modified (non-adhering) or other characteristics than possessed by the substrate material, such an intermittent technique cannot provide such a result, nor can it provide the flexibility of the simultaneous application of different coating materials.

It is to enable such flexibility and novel results, accordingly, that the present invention is directed; it being an object of the invention to provide a new and improved method, apparatus and product, including but not limited to adhesive-non-adhesive section elastic band and diaper assembly and the like, involving co-extruded coating sections of different-characteristic coating materials.

A further object is to provide a novel method and apparatus more generically applicable to co-extruding coating patterns for different material characteristics, applicable not only to hot melt adhesive type coating materials, but to fluid coating materials generally, as well.

Other and further objects will be explained hereinafter and are more particularly delineated in the appended claims.

Figure 2:
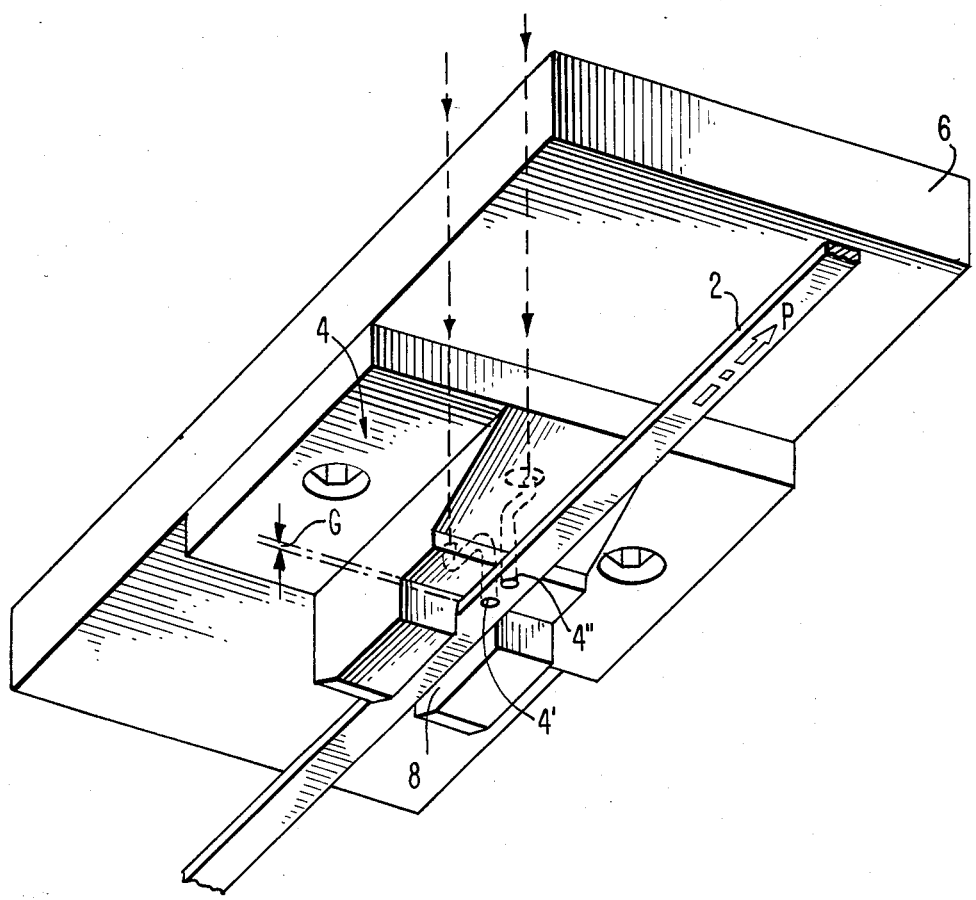
Figure 3:
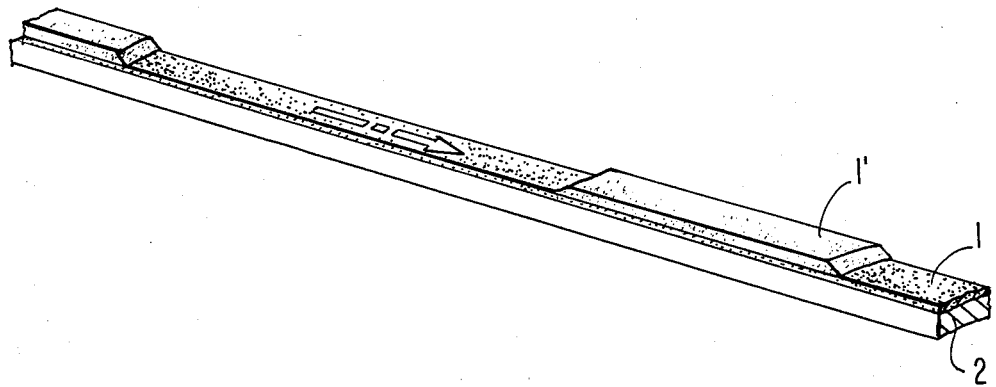

In my earlier U.S. Pat. No. 4,476,165, above-mentioned, co-extrusion apparatus is disclosed that while more generally useful, can be admirably suited to be modified for use in accordance with the present invention. To practice the method of the invention, however, apparatus of the type shown in the accompanying drawing and later described herein, is required;

FIG. 1 being a schematic system diagram of a preferred apparatus for practicing the method underlying the invention;

FIG. 2 is an isometric view, upon and enlarged scale, looking upward from under the co-extrusion nozzle section of FIG. 1; and FIG. 3 is an isometric view, upon still a larger scale, of the nozzle band product produced in this exemplary application of the invention.

In summary, the invention from its more general viewpoint, embraces a method of modifying the physical surface properties of predetermined portions of a continuous layer at which different surface properties are required, that comprises, continuously extruding at a predetermined region upon a band being drawn passed said predetermined region, a layer having the desired physical surface properties, periodically and intermittently co-extruding at a second region just beyond said predetermined region a top layer upon the first-named layer adapted to adhere thereto but presenting said different surface properties, and timing the periodic intermittent co-extrusion to select those predetermined portions of the continuous first-named layer where said different surface properties are desired.

The invention in its more specific hot melt application involves applicating apparatus for co-extrusion of hot melt materials and the like having, in combination, means for feeding a band-to-be-coated along a predetermined path, co-extrusion nozzle means having a pair of dispensing openings disposed at successive closely spaced regions along said predetermined path, means for continuously pumping hot-melt pressure-sensitive adhesive material to the first of said nozzle openings to extrude the same upon the band as a continuous layer, means for periodically and intermittently pumping hot-melt non-adhesive coating material to the second of said nozzle openings during the continuous extrusion from the first opening to extrude a non-adhesive top layer upon the hot melt adhesive layer carried by the band, and means for controlling the timing of the periodic intermittent operation of the co-extrusion means to select those predetermined portions of the continuous hot-melt adhesive layer carried by the band where non-stick characteristics are desired.

Preferred and best mode embodiments and details are hereinafter presented.

Referring to FIG. 1, a co-extrusion adhesive coating system is illustrated as an example of an important application of the invention, operating to provide hot melt pressure-sensitive adhesive coating sections 1 and non-adhering or non-stick coating sections 1' to an elastic band or other substrate 2 shown being drawn past a co-extrusion nozzle applicating or coating head 4. The co-extruder head comprises a pair of nozzles as of the slot type described in the above-cited patents, or conventional bead nozzle openings 4' and 4", as more particularly shown in FIG. 2, one disposed in front of the other at successive closely spaced regions along the direction of the path P of movement of the band under the head 4, extruding their respective coating materials through a porting plate 6 from a plane just above the band, say with an applicating gap G of about 0.004 to 0.006 inch. The band 2 is shown guided in a channel 8 in the direction P under the porting plate 6 past successive nozzle openings 4', 4".

The respective nozzles 4' and 4" are shown supplied through respective 3-way poppet valves 10, 10' (as of the type described in U.S. patent application Ser. No.

509,354, filed 6/30/83, now U.S. Pat. No. 4,565,217, issued Jan. 21, 1986, or other well-known multi-valves), fed by respective coating material supply lines 12, 12' from respective positive displacement metering pumps 14, 14' (as, for example, of the type described in the above-cited patents), pumping the respective coating materials illustratively shown as hot melt pressure-sensitive adhesive material in hopper 16' (filtered at 18') for nozzle 4", and hot melt non-stick material in hopper 16 (filtered at 18) for co-extrusion at nozzle 4'. In the example shown, the adhesive coating (such as pressure-sensitive silicone adhesive) applied by nozzle 4" as a first lyaer 1 on the band 2 at the head 4 is extruded as a continuous layer 1. The metering pump 14' therefor is controlled by a digital motor drive 20' which is connected via line 3' to a reference magnetic signal pick-up sensor 5 for synchronizing the pump drive speed to the web speed of the band 2 as determined by the band feed drive rolls 7. A similar digital motor drive 20 controls the metering pump 14 of the non-stick coating material for nozzle 4', with synchronization control via line 3 to the sensor 5, with the 3-way poppet valve 10 being periodically intermittently shuttered by the intermittent electronic control circuit 9 via control line 9'. The regions where the non-adhering characteristics of the nozzle 4' coating material are desired are therefore periodically selected, and the desired non-stick top layer sections 1' are co-extruded upon the adhesive layer 1 on the band at such regions, as more particularly shown in the enlarged view of FIG. 3.

For the elastic band diaper (or similar) applications, before described, desired non-adhering characteristics are provided at 1', terminating both ends of the central outer layer laminating region 1 at which the pressure-sensitive adhesive coating is exposed, with the advantages previously described. As before explained, during the assembly of the finished diaper, the pressure-sensitive adhesive section 1 is laminated to the polyethylene or other outer web covering; and by providing the "non-stick" top coated sections 1' before and after the section 1, areas of the diaper outside this center of the longitudinal length of the diaper will not be sticky.

More generally, with the technique of the invention, co-extruded layer sections 1' may impart any desired physical characteristics of the selected material of coating supply line 12 to the very different material characteristics of coating material 1 from supply line 12' extruded first upon the band 2.

As before indicated, the invention is useful with a wide variety of fluid coatings, including those specified in said patents and others, ranging from room-temperature to hot melt coatings, and others, and certainly other substrate products than elastic bands for diapers are readily producible by the invention with the same or similar advantages; further modifications occurring to those skilled in the art being therefore considered to fall within the spirit and scope of the invention as defined in the appended claims.

What is claimed is:

1. A method of rendering predetermined portions of a continuous pressure-sensitive hot melt adhesive layer non-adhering, that comprises, continuously extruding hot-melt pressure-sensitive adhesive at a predetermined region as a continuous layer upon a band being drawn past said predetermined region, periodically and intermittently co-extruding at a second region just beyond said predetermined region a hot-melt non-adhering material as discrete, spaced, top layer sections permanently attached to the continuous hot melt adhesive layer, and timing the periodic intermittent co-extrusion to select those predetermined portions of the continuous hot-melt adhesive layer where non-stick characteristics are desired.

2. An elastic band for diaper lamination and similar applications having a continuous adhered coating layer of pressure sensitive adhesive terminated at its end sections with discrete, spaced top coating sections of non-stick coating layers coextruded upon and permanently attached to the continuous adhesive layer.

3. A method of providing an elastic band for diaper lamination and similar applications with a continuous adhered coating of adhesive and spaced non-adhering regions, comprising extruding a continuous layer of adhesive material upon a band being drawn past a predetermined location, and periodically and intermittently co-extruding upon said continuous layer, at a second location just beyond said predetermined location, discrete, spaced, top layer sections of a material that is permanently attached to the material of said continuous layer and that is non-adhering to other materials.

* * * * *